(12) United States Patent
Yabuta et al.

(10) Patent No.: US 8,637,544 B2
(45) Date of Patent: Jan. 28, 2014

(54) NEURITE FORMATION PROMOTER

(75) Inventors: Chiho Yabuta, Hyogo (JP); Fumiko Yano, Hyogo (JP); Mitsuyoshi Azuma, Hyogo (JP)

(73) Assignees: Senju Pharmaceutical Co., Ltd., Osaka (JP); Astellas Pharma Inc., Tokyo (JP)

( * ) Notice: Subject to any disclaimer, the term of this patent is extended or adjusted under 35 U.S.C. 154(b) by 0 days.

(21) Appl. No.: 12/596,581

(22) PCT Filed: Apr. 18, 2008

(86) PCT No.: PCT/JP2008/057583
§ 371 (c)(1),
(2), (4) Date: Jan. 29, 2010

(87) PCT Pub. No.: WO2008/133198
PCT Pub. Date: Nov. 6, 2008

(65) Prior Publication Data
US 2010/0144792 A1 Jun. 10, 2010

(30) Foreign Application Priority Data
Apr. 20, 2007 (JP) ................................ 2007-112248

(51) Int. Cl.
*A61K 31/445* (2006.01)

(52) U.S. Cl.
USPC ........................................ 514/317; 514/912

(58) Field of Classification Search
USPC ................................ 514/317, 912
See application file for complete search history.

(56) References Cited

U.S. PATENT DOCUMENTS

| 2003/0118576 A1 | 6/2003 | Brancato et al. |
| 2006/0069104 A1 | 3/2006 | Matsuda et al. |
| 2006/0234922 A1 * | 10/2006 | Takayama et al. ................ 514/9 |

FOREIGN PATENT DOCUMENTS

| EP | 1 566 184 A1 | 8/2005 |
| WO | WO 00/42011 A1 | 7/2000 |
| WO | WO 00/72834 A2 | 12/2000 |
| WO | WO 03/084542 A1 | 10/2003 |
| WO | WO 2004/039403 A1 | 5/2004 |
| WO | WO 2007/104035 A1 | 9/2007 |

OTHER PUBLICATIONS

Ang et al., *Current Opinion in Ophtalmology*, 12: 318-322 (2001).
Bragheeth et al., *Br. J. Ophthalmol*, 89(5): 580-585 (2005).
Linna et al., *Exp. Eye Res.*, 66: 755-763 (1998).
Linna et al., *Investigative Ophthalmology & Visual Science*, 41(2): 393-397 (2000).
Solomon et al., *The Ocular Surface*, 2(1): 34-42 (2004).
Tokita et al., *European Journal of Pharmacology*, 527:111-120 (2005).
Xu et al., *Cornea*, 15(3): 235-239 (1996).
European Patent Office, Extended European Search Report for European Application No. 08740638.2 (Feb. 28, 2011).
Tokita et al., *Eur. J. Pharmacol.*, 527: 111-120 (2005).

\* cited by examiner

*Primary Examiner* — Zohreh Fay
(74) *Attorney, Agent, or Firm* — Leydig, Voit & Mayer, Ltd.

(57) ABSTRACT

The invention provides an agent for promoting ocular tissue neuritogenesis, containing N-(1-acetylpiperidin-4-yl)-4-fluorobenzamide or a pharmaceutically acceptable salt thereof, and an agent for promoting corneal neuritogenesis and retinal neuritogenesis, containing N-(1-acetylpiperidin-4-yl)-4-fluorobenzamide or a pharmaceutically acceptable salt thereof. The corneal neuritogenesis promoter can be used for the improvement of corneal sensitivity, treatment of dry eye, or treatment of a corneal epithelial disorder. The retinal neuritogenesis promoter can be used for the improvement of a visual dysfunction.

11 Claims, 2 Drawing Sheets

NEURITE FORMATION PROMOTER

TECHNICAL FIELD

The present invention relates to a neurite formation promoter. Specifically, the present invention relates to an agent for the improvement of corneal sensitivity or visual function based on the promotion of neuritogenesis by an amide compound.

BACKGROUND ART

Since corneal nerve is severed by corneal surgeries such as laser photorefractive keratectomy (PRK), laser-assisted-in-situ keratomileusis (LASIK), laser epithelial keratomileusis (LASEK) and keratoplasty, the corneal sensitivity does not recover generally for about 3 weeks to 1 year. It has been reported, for example, that after LASIK, the corneal nerve is apparently severed (Non-patent Document 1), and that corneal sensitivity decreases in a corneal region where, after LASIK, neurogram is not observed or the nerve bundle is too short to create connection (Non-patent Document 2).

It has been demonstrated that the corneal hyposensitivity after PRK and LASIK causes lower lacrimal gland responses and decreased lacrimal fluid (Non-patent Document 3). As a result of the functional decrease of corneal sensitivity, patients after a corneal surgery blink less number of times, problematically showing the symptoms of dry eye. In dry eye patients, lacrimal hypofunction gives rise to pathological changes in the corneal epithelium and decreased corneal sensitivity (Non-patent Document 4). Specifically, it is problematic that decreased corneal sensitivity diminishes lacrimation and makes corneal surface symptoms severe. Other reports state that corneal wound cure is hampered due to dry eyes caused by PRK and LASIK (Non-patent Document 3), and that recurrent corneal erosions were observed after LASIK surgery (Non-patent Document 5).

At present, however, recovery of corneal sensitivity that has decreased after a corneal surgery is left to spontaneous recovery, and no active treatment is provided to recover corneal sensitivity in the treatment of dry eyes. In addition, corneal hyposensitivity is caused by the diseases accompanying corneal neurodegeneration, such as neuroparalytic keratopathy, corneal ulcer, and diabetic keratopathy, but no appropriate therapies are available. Regarding corneal nerves, it has been reported that the nerves derived from the first branch (ophthalmic branch) that bifurcates at the trigeminal ganglion are mostly distributed in the cornea and profoundly involved in postoperative restoration of corneal sensation, repair of corneal epithelium, and the like (Non-patent Document 4).

Retinal ganglion cells are the output cells of the retina; the neurites thereof, also called as optic nerve fibers, run in the retinal inner layer and nerve fiber layer (the side closest to the vitreous body) and assemble in the optic disc, then leave the eyeball and form optic nerves, thus playing a role in transmitting visual information to the cerebral cortex. It is known that various retinal diseases, increased intraocular pressure (glaucoma) and the like cause optic nerve atrophy and degeneration, resulting in visual dysfunctions. Drugs that allow the function of the visual information transmission pathway in the retina to be restored, particularly drugs capable of neogenesis and promoted elongation of retinal nerve cell neurites, are possibly useful against these visual dysfunctions.

N-(1-acetylpiperidin-4-yl)-4-fluorobenzamide is a compound exhibiting an enhancing action of the cholinergic activity (Patent Document 1). This amide compound is a compound expected to be useful for treating disorders in mammalian central nervous systems, more specifically of amnesia, dementia and the like. It has also been demonstrated that this amide compound may enhance the release of somatostatin in experiments using rat hippocampal slices, inhibit the calcium influx suppression induced by somatostatin in the rat hippocampal neuron, and improve cognitive dysfunctions via activation of the somatostatin neurotransmission system (Non-patent Document 6, Patent Document 2). It is also known that N-(1-acetylpiperazin-4-yl)-4-fluorobenzamide is used as a promoter for producing a neurotrophic factor (Patent Document 3).

Somatostatin is known to promote neuritogenesis of rabbit trigeminal nerve cell in in vitro experiments, and administration of somatostatin by instillation is known to improve corneal sensitivity function in in vivo tests using rabbits (Patent Document 4, particularly Test Example 2 and Test Example 3). However, N-(1-acetylpiperidin-4-yl)-4-fluorobenzamide is not known to enhance the release of somatostatin in ocular tissue nerve cells, nor to promote neuritogenesis.

patent reference 1: WO2000/042011
patent reference 2: WO2000/072834
patent reference 3: WO2003/084542
patent reference 4: WO2004/039403
non-patent reference 1: Tuuli, U. L. et al., Experimental Eye Research 1998, 66, pp. 755-763
non-patent reference 2: Tuuli, U. L. et al., Investigative Opthalmology & Visual Science 2000, 41, pp. 393-397
non-patent reference 3: Ang, R. T. et al., Current Opinion in Opthalmology 2001, 12, pp. 318-322
non-patent reference 4: Xu, K.-T. et al., Cornea 1996, 15, pp. 235-239
non-patent reference 5: Solomon, R. et al., The Ocular Surface 2004, 2, pp. 34-42
non-patent reference 6: Tokita, K. et al., European Journal of Pharmacology 2005, 527, pp. 111-120

DISCLOSURE OF THE INVENTION

Problems to Be Solved by the Invention

It is an object of the present invention to provide an agent for promoting ocular tissue neuritogenesis. It is another object of the present invention to provide a pharmaceutical use of the ocular tissue neuritogenesis promoter.

Means for Solving the Problems

The present inventors diligently investigated in view of the above-described problems, found that N-(1-acetylpiperidin-4-yl)-4-fluorobenzamide, which had not been known to exhibit any action in trigeminal nerve cells or retinal nerve cells, unexpectedly promotes neuritogenesis, and also found that the same is useful against diseases that accompany ocular tissue neuropathies such as decreased corneal sensitivity via this action, and have completed the present invention. Accordingly, the invention of this application is as follows:

[1] An agent for promoting ocular tissue neuritogenesis, comprising N-(1-acetylpiperidin-4-yl)-4-fluorobenzamide or a pharmaceutically acceptable salt thereof.
[2] An agent for promoting corneal neuritogenesis, comprising N-(1-acetylpiperidin-4-yl)-4-fluorobenzamide or a pharmaceutically acceptable salt thereof.
[3] The agent described in [2] above, which is used for the improvement of corneal sensitivity, treatment of dry eye or treatment of a corneal epithelial disorder.

[4] An agent for promoting retinal neuritogenesis, comprising N-(1-acetylpiperidin-4-yl)-4-fluorobenzamide or a pharmaceutically acceptable salt thereof.

[5] The agent described in [4] above, which is used for the improvement of a visual dysfunction.

[6] A use of N-(1-acetylpiperidin-4-yl)-4-fluorobenzamide or a pharmaceutically acceptable salt thereof for producing an agent for promoting ocular tissue neuritogenesis.

[7] A use of N-(1-acetylpiperidin-4-yl)-4-fluorobenzamide or a pharmaceutically acceptable salt thereof for producing an agent for promoting corneal neuritogenesis.

[8] The use described in [7] above, wherein the agent for promoting corneal neuritogenesis is used for the improvement of corneal sensitivity, treatment of dry eye or treatment of a corneal epithelial disorder.

[9] A use of N-(1-acetylpiperidin-4-yl)-4-fluorobenzamide or a pharmaceutically acceptable salt thereof for producing an agent for promoting retinal neuritogenesis.

[10] The use described in [9] above, wherein the agent for promoting retinal neuritogenesis is used for the improvement of a visual dysfunction.

[11] A method for promoting ocular tissue neuritogenesis, comprising administering an effective amount of N-(1-acetylpiperidin-4-yl)-4-fluorobenzamide or a pharmaceutically acceptable salt thereof to a subject in need of promotion of ocular tissue neuritogenesis.

[12] A method for promoting corneal neuritogenesis, comprising administering an effective amount of N-(1-acetylpiperidin-4-yl)-4-fluorobenzamide or a pharmaceutically acceptable salt thereof to a subject in need of promotion of corneal neuritogenesis.

[13] The method described in [12] above, wherein the method is used for the improvement of corneal sensitivity or treatment of dry eye or a corneal epithelial disorder.

[14] A method for promoting retinal neuritogenesis, comprising administering an effective amount of N-(1-acetylpiperidin-4-yl)-4-fluorobenzamide or a pharmaceutically acceptable salt thereof to a subject in need of promotion of retinal neuritogenesis.

[15] The method described in [14] above, wherein the method is used for the improvement of a visual dysfunction.

EFFECT OF THE INVENTION

Since the pharmaceutical of the present invention, which comprises N-(1-acetylpiperidin-4-yl)-4-fluorobenzamide or a pharmaceutically acceptable salt thereof, has a promoting effect on trigeminal nerve cell neuritogenesis, it is useful for 1) improving decrease in corneal sensitivity caused by corneal nerve damage, and useful for 2) improving decrease in corneal sensitivity associated with corneal epithelial disorder or dry eye. Since the pharmaceutical of the present invention, which comprises N-(1-acetylpiperidin-4-yl)-4-fluorobenzamide or a pharmaceutically acceptable salt thereof, has a promoting effect on retinal nerve cell neuritogenesis, it is also useful for improving a visual dysfunction.

BEST MODE FOR CARRYING OUT THE INVENTION

The present invention provides an agent for promoting ocular tissue neuritogenesis, comprising N-(1-acetylpiperidin-4-yl)-4-fluorobenzamide or a pharmaceutically acceptable salt thereof. The present invention also provides an agent for promoting corneal neuritogenesis and retinal neuritogenesis, comprising N-(1-acetylpiperidin-4-yl)-4-fluorobenzamide or a pharmaceutically acceptable salt thereof. The agent for promoting ocular tissue neuritogenesis and corneal neuritogenesis, the agent for improving corneal sensitivity, the agent for promoting retinal neuritogenesis and the agent for improving visual dysfunction are collectively referred to as the drug of the present invention.

In the present invention, "ocular tissue nerve" means any nerve present in ocular tissue, including a wide variety of nerves, such as the corneal nerve, retinal nerve, oculomotor nerve and ciliary ganglion.

In the present invention, "corneal nerve" means annular plexus formed in the surrounding cornea under the control of the trigeminal nerve, which is a sensory neuron, stroma plexus distributed reticulately in corneal strome, sub-epithelial plexus formed immediately below Bowman's membrane, and basal cell plexus and nerve fiber formed immediately after penetrating Bowman's membrane. In the present invention, "retinal nerve" means the nerve fiber (optic nerve) formed by ganglion cells and the nerve fiber formed by visual cells, bipolar cells, horizontal cells and amacrine cells which are involved in neurotransmission. In the present invention, "neurite" means a protrusion (dendrite and axon) from the cell body of a neuron (nerve cell); "genesis" means an outgrowth and/or extension of the aforementioned neurite from the cell body. In the present invention, "promoting . . . genesis" means an outgrowth and/or extension of the aforementioned neurite from the cell body as caused by the following active ingredient.

N-(1-acetylpiperidin-4-yl)-4-fluorobenzamide ("FK962" CAS No. 283167-06-6), which is contained as an active ingredient in the drug of the present invention, is an amide compound described in the pamphlet of WO2000/042011 (particularly Example 6). A pharmaceutically acceptable salt of this amide compound is a commonly used non-toxic salt. Examples thereof include acid addition salts, for example, inorganic acid addition salts (for example, hydrochlorides, hydrobromides, sulfates, phosphates and the like) and organic acid addition salts (for example, formates, acetates, trifluoroacetates, maleates, tartrates, methanesulfonates, benzenesulfonates, toluenesulfonates and the like), salts with amino acids (for example, aspartates, glutamates and the like), metal salts, for example, alkali metal salts (for example, sodium salts, potassium salts and the like) and alkaline earth metal salts (for example, calcium salts, magnesium salts and the like), and the like.

N-(1-acetylpiperidin-4-yl)-4-fluorobenzamide and a pharmaceutically acceptable salt thereof can be synthesized as described in the pamphlet of WO2000/042011 (particularly Example 6).

The drug of the present invention is useful as a neuritogenesis promoter for ocular tissues such as the corneal nerve and retinal nerve in mammals (for example, humans, mice, rats, hamsters, rabbits, cats, dogs, bovines, sheep, monkeys and the like).

The drug of the present invention is capable of improving the decreased corneal sensitivity caused by corneal nerve damage, severance or defect, by promoting corneal neuritogenesis. Accordingly, the drug of the present invention is useful as a corneal sensitivity improver.

The drug of the present invention is useful as a therapeutic drug that improves the decreased corneal sensitivity associated with diseases that accompany corneal nerve damage, severance or defect, for example, corneal epithelial disorder, dry eye (lacrimal hyposecretion; dry eye of the increased lacrimal fluid evaporation type; Sjogren's syndrome; Stevens-Johnson syndrome; dry eye that accompanies corneal epithelial erosion, marginal blepharitis, ocular pemphigoid, vernal conjunctivitis, allergic conjunctivitis, vitamin A deficiency and the like, and the like), neuroparalytic keratopathy, corneal ulcer, diabetic keratopathy, keratoconjunctivitis (epidemic keratoconjunctivitis, herpes simplex keratitis), keratoconus, corneal degeneration and the like. As mentioned herein, the corneal epithelial disorder means that the corneal epithelium is damaged by an endogenous disease such as corneal ulcer, corneal epithelial detachment, keratoconjunctivitis sicca, chronic superficial keratitis, corneal erosion, or prolonged corneal epithelial defect, by an exogenous disease such as one caused by a drug, trauma, wearing contact lenses or the like, or by a physical or chemical injury. The drug of the present invention is also useful as a therapeutic drug that improves the decreased corneal sensitivity associated with cataract surgery, vitreous surgery, or corneal surgeries such as PRK, LASIK, LASEK or corneal transplantation surgery.

The decreased corneal sensitivity and improvement thereof can be measured by a conventional method using an aesthesiometer such as the Cochet-Bonnet aesthesiometer.

It is known that in dry eye patients, a lacrimal hypofunction gives rise to corneal hyposensitivity, and that this corneal hyposensitivity leads to a further lacrimal hypofunction. It has been reported that this vicious circle aggravates dry eye symptoms, and even causes corneal epithelial disorder. For example, a paper by Mathers (CLAO J. 2000, 26, 159.) reports a "corneal lacrimal gland feedback model" assuming that the lacrimal glands and cornea are tightly integrated in the onset of disease, and that a lacrimal gland disease influences the ocular surface, and an ocular surface disease influences the lacrimal glands. Mathers shows that corneal hyposensitivity induces lacrimal hyposecretion, then leads to a corneal disorder, and, as a result, causes a lacrimal gland disorder, and that these occur in a vicious cycle (particularly on the 39th to 45th lines, right column, page 161). In a paper by Ang et al. (Curr Opin Opthalmol. 2001, 12, 318.), it is stated that decreased corneal sensitivity is a primary cause of corneal epithelial disorders such as superficial punctate keratopathy, resulting in decreased feedback to the lacrimal gland and reduced tear production. In a paper by Xu et al. (Cornea 1996, 15, 235.), it is stated that hyposecretion of tears may lead to morphological changes in corneal epithelium and a decline in corneal sensitivity (for example, lines 44 to 47, right column, page 238). Meanwhile, in a paper by Fujishima et al. (Cornea 1996, 15, 368.), it is suggested that in a study using an aldose reductase inhibitor, an improvement in the dynamics of tear production may be due to an improvement in corneal sensitivity. Therefore, since the drug of the present invention improves the vicious circle of corneal hypesthesia and lacrimal fluid hypofunction by improving corneal hyposensitivity, it is also useful as a therapeutic agent for dry eye or corneal epithelial disorder. Particularly, the drug of the present invention is useful as a therapeutic agent for dry eye or corneal epithelial disorder that accompanies decreased corneal sensitivity.

The drug of the present invention is useful as a therapeutic drug that improves a visual dysfunction caused by retinal nerve damage, severance, degeneration or defect by outgrowth of retinal neurites. Accordingly, the drug of the present invention is useful as an agent for improving a visual dysfunction. In the present invention, the visual dysfunction means a diminishment of retinal ganglion cells or optic nerve fibers due to retinal nerve or optic nerve damage, degeneration and the like; loss of vision, visual acuity reduction, narrowing of visual field, defective color vision or blurred vision that results from optic atrophy, loss of nerve fiber axons, dropping of optic nerve fiber medullary sheath, optic nerve defect and the like; and visual impairment with various symptoms such as abnormalities in electroretinogram and visual evoked potential.

The drug of the present invention is useful as a therapeutic drug that improves a visual dysfunction associated with optic neuritis, optic disc capillary hemangioma, ischemic optic neuropathy, retinal nerve fiber layer defect, retinal optic atrophy, division of optic nerve, traumatic optic neuropathy, papilledema, optic disc defect, optic nerve hypoplasia, toxic optic atrophy, glaucoma and the like.

The drug of the present invention is useful as a therapeutic drug that improves a visual dysfunction associated with retinal inflammation, such as retinal nerve diseases, retinal vascular occlusion, retinal periphlebitis, Eales disease, ischemic ocular syndrome, retinal arteriolar macroaneurysm, retinopathies due to hypertension and renal disease and hematological disease, diabetic retinopathy, retinal dystrophy, macular dystrophy, retinochoroidopathy, macular degeneration, macular edema, retinal pigment epithelial detachment, degenerative retinoschisis, retinoblastoma, and retinal pigment epithelioma. Furthermore, the drug of the present invention is effective for the growth and functional maintenance of visual cells, including retinal ganglion cells, in retinal transplantation, and in optic nerve regeneration in optic nerve transplantation.

The drug of the present invention can be administered to patients orally or parenterally; as modes of administration thereof, oral administration, ocular topical administration (instillation administration, intravitreous administration, subconjunctival administration, administration under Tenon's capsule, and the like), intravenous administration, transdermal administration and the like can be mentioned, and, when required, the drug of the present invention, along with a pharmaceutically acceptable additive, may be prepared as a dosage form suitable for administration. As examples of dosage forms suitable for oral administration, tablets, capsules, granules, powders and the like can be mentioned; as examples of dosage forms suitable for parenteral administration, ophthalmic drops, ophthalmic ointments, injections, patches, lotions, creams and the like can be mentioned. These can be prepared using an ordinary technique in common use in the art. In addition to these preparations, this compound can also be prepared in the form of DDS (drug delivery system) preparations, such as preparations for intraocular implants and microspheres. While the drug of the present invention is not particularly limited as to the route of administration thereof, as far as a therapeutic effect described above is obtained, the drug is preferably given by ocular topical administration. As examples of dosage forms for ocular topical administration, ophthalmic drops and ophthalmic ointments can be mentioned.

As subjects of administration of the drug of the present invention, mammals (for example, humans, mice, rats, hamsters, rabbits, cats, dogs, bovines, sheep, monkeys and the like) can be mentioned.

For example, when the drug of the present invention is used as ophthalmic solutions or ophthalmic ointments, stabilizers (for example, sodium hydrogen sulfite, sodium thiosulfate, sodium edetate, sodium citrate, ascorbic acid, dibutylhydroxytoluene and the like), solubilizers (for example, glycerin, propylene glycol, macrogol, polyoxyethylene hardened castor oil and the like), suspending agents (for example, polyvinylpyrrolidone, hydroxypropylmethylcellulose, hydroxymethylcellulose, carboxymethylcellulose sodium and the like), emulsifiers (for example, polyvinylpyrrolidone, soybean lecithin, egg yolk lecithin, polyoxyethylene hardened castor oil, Polysorbate 80 and the like), buffers (for example, phosphate buffer solution, acetate buffer solution, borate buffer solution, carbonate buffer solution, citrate buffer solution, Tris buffer solution, glutamic acid, epsilon aminocaproic acid and the like), tackifiers (for example, water-soluble cellulose derivatives such as methylcellulose, hydroxyethylcellulose, hydroxypropylmethylcellulose, and carboxymethylcellulose, sodium chondroitin sulfate, sodium hyaluronate, carboxyvinyl polymer, polyvinyl alcohol, polyvinylpyrrolidone, macrogol and the like), preservatives (for example, benzalkonium chloride, benzethonium chloride, chlorhexidine gluconate, chlorobutanol, benzyl alcohol, sodium dehydroacetate, para-oxybenzoates, sodium edetate, boric acid and, the like), isotonizing agents (for example, sodium chloride, potassium chloride, glycerin, mannitol, sorbitol, boric acid, glucose, propylene glycol and the like), pH regulators (for example, hydrochloric acid, sodium hydroxide, phosphoric acid, acetic acid and the like), refreshing agents (for example, l-menthol, d-camphor, d-borneol, peppermint oil and the like), ointment bases (white petrolatum, purified lanolin, liquid paraffin, vegetable oils (olive oil, camellia oil, peanut oil, and the like) and the like) and the like can be added as additives. While the amounts of these additives to be used vary depending on the kind, use and the like of the additives to be used, the additives only need to be added at concentrations capable of achieving the object of the additives.

When the drug of the present invention is prepared as an ophthalmic solution or ophthalmic ointment, the preparation may be produced according to a method in common use in the pharmaceutical field; for example, the preparation can be produced on the basis of the methods described in the Ophthalmic Solutions section and the Ophthalmic Ointments section, General Rules for Preparations, Japanese Pharmacopoeia XV.

The present invention also provides a use of N-(1-acetylpiperidin-4-yl)-4-fluorobenzamide or a pharmaceutically acceptable salt thereof for producing the drug of the present invention.

The dosage of the drug of the present invention varies depending on the target disease, and cannot be generalized; however, it can be set to such an amount that affords the drug concentration in the target tissue where the desired effect is to be exhibited of 0.001 nM (0.26 pg/mL, based on N-(1-acetylpiperidin-4-yl)-4-fluorobenzamide; the same applies below) to 1000 nM (260 ng/mL), preferably 0.001 nM (0.26 pg/mL) to 10 nM (2.6 ng/mL), more preferably 0.01 nM (0.0026 ng/mL) to 1 nM (0.26 ng/mL), and still more preferably 0.05 nM (0.013 ng/mL) to 0.5 nM (0.13 ng/mL).

When the drug of the present invention is topically used for adult eyes as a corneal sensitivity improver, it is recommended that an ophthalmic solution containing 0.01 nM (0.0026 ng/mL) to 100 nM (26 ng/mL), preferably 0.1 nM (0.026 ng/mL) to 10 nM (2.6 ng/mL), and more preferably 0.5 nM (0.13 ng/mL) to 5 nM (1.3 ng/mL), of the active ingredient, about 20 to about 50 μL per dose, be instilled 1 to 8 times, preferably 1 to 5 times, a day.

Since the drug of the present invention is active in promoting ocular tissue neuritogenesis, promoting corneal neuritogenesis, or promoting retinal neuritogenesis, the present invention also provides a method of promoting ocular tissue neuritogenesis, corneal neuritogenesis or retinal neuritogenesis, comprising administering an effective amount of N-(1-acetylpiperidin-4-yl)-4-fluorobenzamide or a pharmaceutically acceptable salt thereof to a subject in need of such promotion.

As subjects of a method of promotion of the present invention, mammals (for example, humans, mice, rats, hamsters, rabbits, cats, dogs, bovines, sheep, monkeys and the like) can be mentioned, humans being preferable.

Method of administration, dosage form, and dosage of N-(1-acetylpiperidin-4-yl)-4-fluorobenzamide or a pharmaceutically acceptable salt thereof being an active ingredient in the method of promotion of the present invention can be set as appropriate as described above with respect to the drug of the present invention.

The method of the present invention for promoting corneal neuritogenesis is preferably used for the improvement of corneal sensitivity, treatment of dry eye or treatment of a corneal epithelial disorder.

The method of the present invention for promoting retinal neuritogenesis is preferably used for the improvement of a visual dysfunction.

EXAMPLES

The present invention is hereinafter described in further detail by means of the following examples, to which, however, the invention is not limited.

Test Example 1

Promoting Effect on Neuritogenesis in Cultured Rabbit Trigeminal Nerve Cells

1. Animals Used

Japanese White rabbits (4 days old, male) purchased from Oriental Yeast Co., Ltd. were used.

2. Test Substance

N-(1-acetylpiperidin-4-yl)-4-fluorobenzamide (hereinafter referred to as Compound A) was used.

3. Test Procedures

A) Cell Culture

Rabbit trigeminal nerve cells were isolated according to the report of Chan et al. (Kwan Y. Chan and Richard H. Haschke. Exp. Eye Res. 41: 687-699, 1985). Specifically, a rabbit underwent cardiac perfusion with physiological saline under anesthesia with pentobarbital sodium injection (Dainippon Sumitomo Pharma), after which the trigeminal ganglia thereof were cut out. The trigeminal ganglia cut out were washed with Hanks' balanced salt solution (HBSS, Invitrogen), and thereafter treated with 300 μg/mL collagenase-dispase (Roche) at 37° C. for 40 minutes; centrifugation was performed at 120×g for 5 minutes, and the cells were collected. The enzyme reaction was stopped with Neurobasal (registered trademark, Invitrogen) supplemented with EDTA at a final concentration of 0.1%, and the cells were suspended in culture medium, after which centrifugation was performed at 120×g for 5 minutes, and trigeminal nerve cells were prepared.

The cells prepared were seeded in a 8-well chamber slide coated with polylysine/laminin (Falcon) at about 3×10³ cells/well; after the seeding, the cells were cultured for 24 hours. After 24 hours of culture, each of Compound A (final concentration 0.1 nM (0.026 ng/mL)) and NGF (final concentration 1 μg/mL) as a positive control or PBS as a control was added to the culture medium. After the addition, the cells were further cultured for 48 hours.

The culture medium used was a Neurobasal containing the B27 supplement (Invitrogen) (final concentration 2% (v/v)), L-glutamine (Invitrogen) (final concentration 1 mM) and cytosine-1-β-D(+)arabinofuranoside (final concentration 10 μM). Culturing conditions were set at a carbon dioxide concentration of 5%, an air concentration of 95%, a humidity of 100%, and a temperature of 37° C.

B) Staining

After the 48 hours of cultivation following the addition, the rabbit trigeminal nerve cells were immersed and fixed in 10% neutrally buffered formaldehyde solution at room temperature for 20 minutes. The specimens fixed were fluorescently stained using the anti-neurofilament 200 antibody (Sigma-Aldrich), which specifically recognizes neurofilaments constituting nerve cell bodies and neurites, and the cells stained were examined under a fluorescence microscope (Olympus). Stained cell were incorporated as images from the fluorescence microscope into a computer.

C) Image Analysis

To evaluate the degree of neuritogenesis in the cultured rabbit trigeminal nerve cells, cell body diameters and neurite lengths were measured on the computer-captured stained cell images using image analysis software (Image-Pro Plus Ver. 4.5.1, Media Cybernetics). Cells having a neurite with a length of not less than twice the diameter of the cell body were regarded as neuritogenesis cell, and the ratio (%) of the cells to the total cell count was calculated (Otori Y, Wei J Y, Barnstable C J. Invest. Opthalmol V is Sci (1998) 39, 972-981).

4. Test Results

Figure 1:
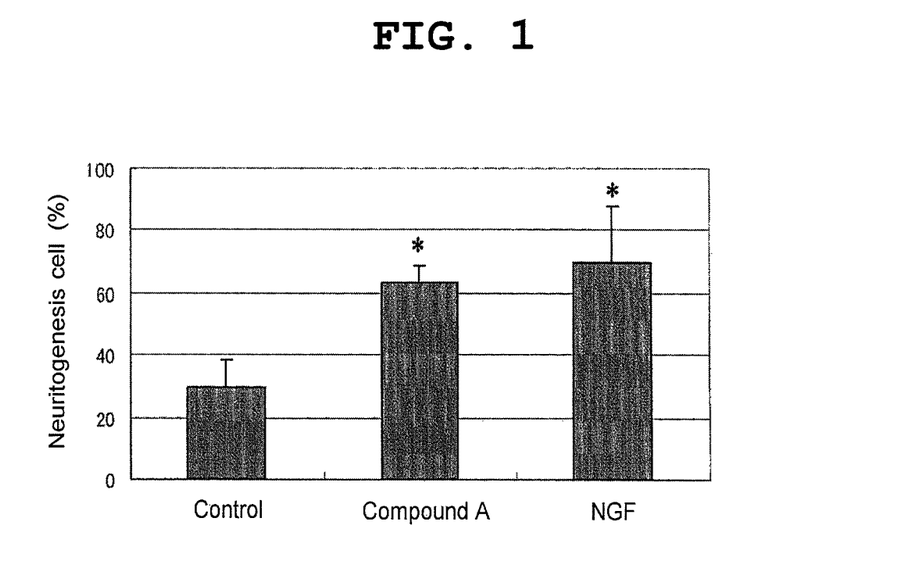
FIG. 1 shows the ratio (%) of neuritogenesis cells to all cells. The axis of ordinates indicates the percentage of neuritogenesis cells to all cells. In this figure, * indicates a significant difference ($p<0.005$) from a control group.

FIG. 1 is a graph showing the ratio (%) of neuritogenesis cells to all cells. The ratio of neuritogenesis cells was 29.5±8.7% for the control group, 63.3±5.2% for the 0.1 nM Compound A addition group, and 70.0±17.6% for the NGF addition group. Statistical analysis revealed significant promoting effect on neuritogenesis in both the 0.1 nM Compound A addition group and the NGF addition group, compared with the control group (N=6, 5, 5 (arranged in the same order), mean±standard deviation, *: p<0.005; Dunnett's multiple comparison test).

These results demonstrated that Compound A has promoting effect on neuritogenesis in cultured rabbit trigeminal nerve cells. Furthermore, Compound A has promoting effect on neuritogenesis in trigeminal nerve cells at lower concentrations than did NGF (1 μg/mL), which is generally used as a positive control.

Test Example 2

Promoting Effect on Neuritogenesis in Rabbit Retinal Cells

1. Animals Used

Japanese White rabbits (4 days old, male) purchased from Oriental Yeast Co., Ltd. were used.

2. Test Substance

Compound A was used.

3. Testing Procedures

1) Cell Culture

A rabbit underwent cardiac perfusion with physiological saline under anesthesia with pentobarbital sodium injection (Dainippon Sumitomo Pharma), after which the eyeballs were extirpated and the retinas were isolated. The retinas isolated were placed in a papain solution (1 mg/mL, Sigma-Aldrich Japan K.K.) suspended in Hanks' balanced salt solution (HBSS, Invitrogen), and subjected to enzymatic digestion at 37° C. for 30 minutes. Thereafter, Leibovitz's L-15 Medium (L-15, Invitrogen) was used to prepare reagents. After the suspension was allowed to stand, the supernatant was discarded, 3 mL of a trypsin inhibitor solution (2 mg/mL trypsin inhibitor, 0.004% DNase and 1 mg/mL Bovine Serum Albumin dissolved in L-15, pH 7.4) was added, and pipetting was performed. After the solution was allowed to stand, the supernatant was discarded, another 3 mL of the trypsin inhibitor solution was added, pipetting was performed, and this operation was once again repeated; centrifugation was performed at 120×g for 5 minutes, and the supernatant was removed. 2 ml of a high concentration trypsin inhibitor solution (10 mg/mL trypsin inhibitor, 10 mg/mL Bovine Serum Albumin dissolved in L-15, pH 7.4) was added, and pipetting was performed; centrifugation was performed at 120×g for 5 minutes, and the supernatant was discarded. The cells were suspended in 10 mL of an L-15 solution (Invitrogen) containing 0.05% Bovine Serum Albumin (BSA), and anti-macrophage antibody was added (final concentration 1 μg/mL). After incubation at room temperature for 20 minutes, centrifugation was performed at 120×g for 5 minutes, the supernatant was discarded, and the cells were suspended in 20 mL of 0.05% BSA/L-15, and seeded in a dish previously coated with a secondary antibody (anti-mouse IgG antibody, Nippon Chemi-Con). After incubation at 37° C. for 40 minutes, the suspending cell solution was centrifuged at 120×g for 5 minutes, whereby the cells were collected. The cells were seeded in a 8-well chamber slide coated with polylysine/laminin (Falcon) at about 3×10³ cells/well; after the seeding, the cells were cultured for 24 hours. After 24 hours of culture, each of Compound A (final concentration 0.1 nM (0.026 ng/mL)) and NGF (final concentration 1 μg/mL) as a positive control or PBS as a control was added to the culture medium. After the addition, the cells were further cultured for 48 hours. The culture medium used was a Neurobasal containing the B27 supplement (Invitrogen) (final concentration 2% (v/v)), L-glutamine (Invitrogen) (final concentration 1 mM) and cytosine-1-β-D(+)arabinofuranoside (final concentration 10 μM). Culturing conditions were set at a carbon dioxide concentration of 5%, an air concentration of 95%, a humidity of 100%, and a temperature of 37° C.

2) Staining

The cells were stained in the same manner as Test Example 1.

4. Test Results

Figure 2:
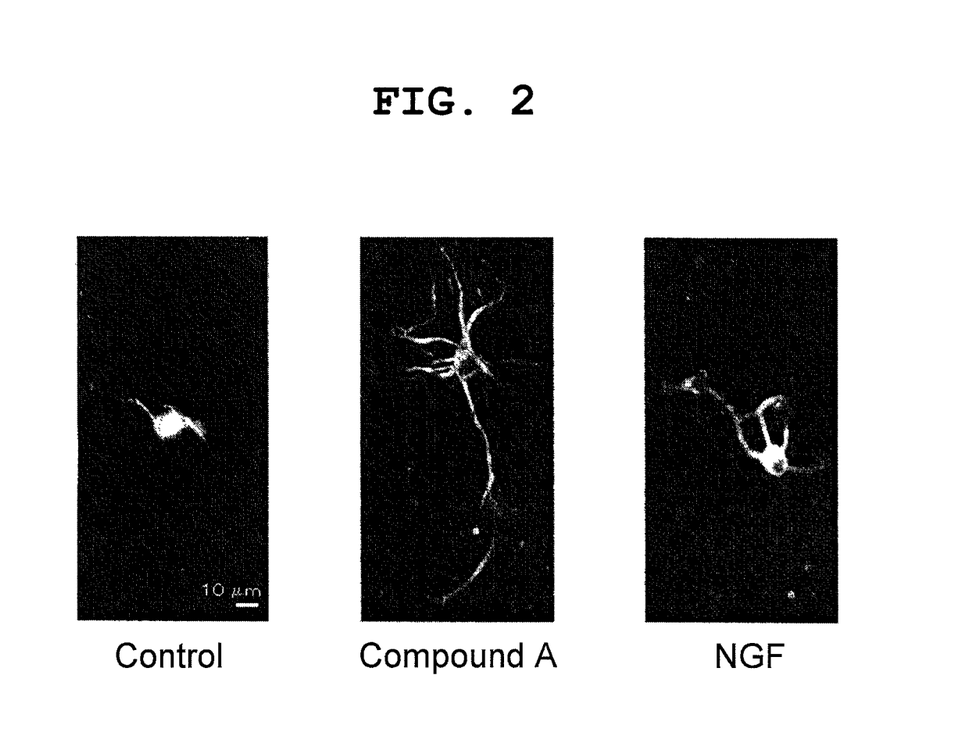
FIG. 2 is a photographic representation of retinal nerve cells stained with anti-neurofilament antibody.

Results are shown in FIG. 2. FIG. 2 is a photographic representation of retinal nerve cells stained with anti-neurofilament antibody. Remarkable neuritogenesis was observed in the cells with the addition of Compound A.

Preparation Example

1 Eye Drops

| | |
|---|---|
| Compound A | 0.026 μg |
| Polysorbate 80 | 0.1 g |
| Sodium dihydrogen phosphate | 0.1 g |
| Sodium chloride | 0.9 g |
| Benzalkonium chloride | 0.005 g |
| Sodium hydroxide | q.s. |
| Sterile purified water | q.s. |
| Total quantity 100 mL (pH 7.0) | |

These ingredients are blended to obtain eye drops.

Preparation Example 2

Eye Ointment

| | |
|---|---|
| Compound A | 1 μg |
| Purified lanolin | 10 g |
| White petrolatum | 100 g |

These ingredients are blended to obtain an eye ointment.

Test Example 3

Promoting Effect on Neuritogenesis in Cultured Rabbit Trigeminal Nerve Cells

1. Animals Used
Japanese White rabbits (4 days old, male) purchased from Oriental Yeast Co., Ltd. were used.
2. Test Substance
Compound A was used.
3. Test Procedures
A) Cell Culture
Rabbit trigeminal nerve cells were isolated according to the report by Chan et al. (Kwan Y. Chan and Richard H. Haschke. Exp. Eye Res. 41: 687-699, 1985). Specifically, a rabbit underwent cardiac perfusion with physiological saline under anesthesia with pentobarbital sodium injection (Dainippon Sumitomo Pharma), after which the trigeminal ganglia were cut out. The trigeminal ganglia cut out were washed with Hanks' balanced salt solution (HBSS, Invitrogen), and thereafter treated with 300 μg/mL collagenase-dispase (Roche) at 37° C. for 40 minutes; centrifugation was performed at 120×g for 5 minutes, and the cells were collected. The enzyme reaction was stopped with Neurobasal (registered trademark, Invitrogen) supplemented with EDTA at a final concentration of 0.1%, and the cells were suspended in culture medium, after which centrifugation was performed at 120×g for 5 minutes, and trigeminal nerve cells were prepared.

The cells prepared were seeded in a 8-well chamber slide coated with polylysine/laminin (Falcon) at about $3 \times 10^3$ cells/well; after the seeding, the cells were cultured for 24 hours. After the 24 hours, each of Compound A (final concentration: 0.001 nM (0.00026 ng/mL), 0.1 nM (0.026 ng/ml), 10 nM (2.6 ng/mL), 1000 nM (260 ng/mL)) and NGF (final concentration 1 μg/ml) as a positive control or PBS as a control, was added to the culture medium. After the addition, the cells were further cultured for 48 hours.

The culture medium used was a Neurobasal containing the B27 supplement (Invitrogen) (final concentration 2% (v/v)), L-glutamine (Invitrogen) (final concentration 1 mM) and cytosine-1-β-D(+)arabinofuranoside (final concentration 10 μM). Culturing conditions were set at a carbon dioxide concentration of 5%, an air concentration of 95%, a humidity of 100%, and a temperature of 37° C.

B) Staining
After the 48 hours of cultivation, the rabbit trigeminal nerve cells were immersed and fixed in 10% neutrally buffered formaldehyde solution at room temperature for 20 minutes. The specimens fixed were fluorescently stained using the anti-neurofilament 200 antibody (Sigma-Aldrich), which specifically recognizes neurofilaments constituting nerve cell bodies and neurites, and the cells stained were examined under a fluorescence microscope (Olympus). Stained cells were incorporated as images from the fluorescence microscope into a computer.

C) Image Analysis
To evaluate the degree of neuritogenesis in the cultured rabbit trigeminal nerve cells, cell body diameters and neurite lengths were measured on the computer-captured stained cell images using image analysis software (Image-Pro Plus Ver. 4.5.1, Media Cybernetics). Cells having a neurite with a length of not less than twice the diameter of the cell body were regarded as neuritogenesis cells, and the ratio (%) of the cells to the total cell count was calculated (Otori Y, Wei J Y, Barnstable C J. Invest. Opthalmol V is Sci (1998) 39, 972-981).

4. Test Results
Table 1 shows the ratio (%) of neuritogenesis cells to all cells. In all of the 0.001 nM, 0.1 nM, 10 nM, and 1000 nM Compound A addition groups, the ratio (%) of neuritogenesis cells was higher than in the control group. Statistical analysis revealed significant promoting effect on neuritogenesis in both the 0.1 nM Compound A addition group and the NGF addition group, compared with the control group (mean±standard deviation, *: $p<0.05$; Dunnett's multiple comparison test).

Judging from the results shown above, Compound A exhibited promoting effect on neuritogenesis in trigeminal nerve cells at lower concentrations than NGF (1 μg/mL), which is generally used as a positive control, with 0.1 nM being the optimum concentration.

TABLE 1

| | Ratio (%) of neuritogenesis cells |
|---|---|
| 0.001 nM Compound A | 33.6 ± 16.3 |
| 0.1 nM Compound A | 45.9 ± 15.1* |
| 10 nM Compound A | 37.2 ± 16.5 |
| 1000 nM Compound A | 37.0 ± 20.0 |
| NGF (1 μg/mL) | 47.3 ± 15.9* |
| Control | 30.4 ± 19.5 |

Test Example 4

Improving Effect on Rabbit Corneal Hyposensitivity

1. Animals Used
Japanese White rabbits weighing 2.5 to 3.0 kg purchased from KITAYAMA LABES were used. From arrival to the day of test completion, the animals were kept in a breeding room set at a room temperature of 23±3° C., a humidity of 55±10%, and 12-hour lighting (lighted on at 8:00, lighted off at 20:00) at one animal per cage. Each animal was fed up to 100 to 120 g of a solid food (Labo R Stock, Nosan Corporation) a day, and had free access to tap water.

2. Test Substance

Compound A was used as a test substance. The test substance was dissolved in the base shown below to obtain a concentration of 1 nM (0.00000026%) to yield an ophthalmic solution. For a control group, the following base, free of the test substance, was administered by instillation.

Base Formulation:

| | |
|---|---|
| Sodium dihydrogen phosphate dihydrate | 0.1 g |
| Sodium chloride | 0.9 g |
| Sodium hydroxide | q.s. |
| Purified water | q.s. |
| | 100 mL (pH 7.0) |

3. Test Procedures

1) Grouping

On the day before flap creation, the animals were macroscopically examined for the ocular surface and examined for fluorescein-stained spots in the cornea; rabbits with no abnormalities observed therein were selected, and initial values of corneal sensitivity were measured using the Cochet-Bonnet aesthesiometer (manufactured by Luneau). To uniformize the distribution of initial values of corneal sensitivity, the animals were grouped by the univariate complete randomization technique using the SAS preclinical package (Version 5.0, SAS Institute Japan).

2) Creation of Corneal Flap

Each animal underwent general anesthesia by intramuscular injection (0.9 mL/kg) of a mixed solution (0.5:1) of Celactal (2% xylazine: Bayer Japan) and Ketalar (5% ketamine for intramuscular injection: Daiichi Sankyo). After each eyeball was thoroughly exteriorized, a corneal flap 130 µm in thickness and 8.5 mm in diameter was created using a microkeratome (MK-2000, NIDEK) equipped with an adapter for rabbit eyes (Arbelaez M C. et al. J. Refract Surg. 2002 May-June; 18(3 Suppl):S357-60). The flap was returned exactly to the original position under a microscope, and the animal awoke from the anesthesia while being carefully watched not to dislocate the flap. After awakening, 0.3% gatifloxacin ophthalmic solution (Gatiflo Ophthalmic Solution, Senju Pharmaceutical) was administered.

3) Administration

On the day after flap creation, individuals not exhibiting flap detachment were given the test substance ophthalmic solution or base by instillation for 6 weeks. The administration by instillation was performed on the operated eye at 2-hour intervals four times a day at 50 µL per dose using a micropipet. For 6 days after surgery, 0.3% gatifloxacin ophthalmic solution was administered before instillation of the test substance ophthalmic solution or vehicle.

4) Corneal Aesthesiometry

One week, 2 weeks, 4 weeks or 6 weeks after surgery, corneal sensitivity was measured using the Cochet-Bonnet aesthesiometer. The tester involved in the measurements was blinded to be unaware of the group to which the subject rabbit belongs.

5. Test Results

Figure 3:
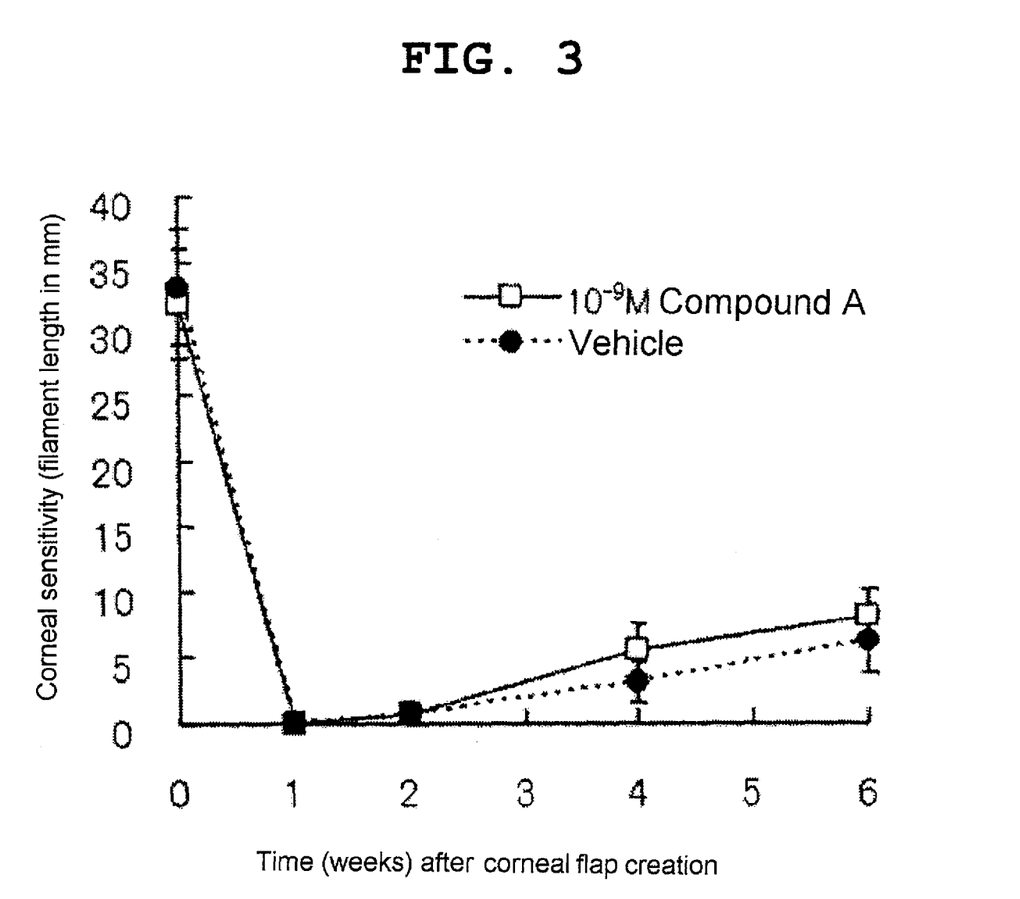
FIG. 3 is a graph showing changes over time in corneal sensitivity after creation of corneal flap.

FIG. 3 shows changes over time in corneal sensitivity after creation of the corneal flap. In the vehicle instillation group, 1 week after corneal flap creation, all individuals lost their sense, after which, however, their sense was restored over time to the 6th week. In contrast, in the drug liquid instillation group, 1 week after corneal flap creation, all individuals lost their sense; however, after the 4th week, the group tended to show accelerated recovery than the vehicle instillation group.

Comparing the times when a sense was observed for the first time after corneal flap creation (the first time when a measured value of 5 mm in filament length or more for sensitivity to anesthesia was obtained), the time was 5.5 weeks on average for the vehicle instillation group, and 4.1 weeks on average for the drug liquid instillation group. From these findings, it was found that the drug liquid instillation group showed an accelerated recovery from decreased corneal sensitivity after flap creation.

INDUSTRIAL APPLICABILITY

The drug of the present invention is useful for 1) improving decreased corneal sensitivity caused by corneal nerve damage, and 2) improving decreased corneal sensitivity that accompanies corneal epithelial disorder or dry eye. The drug of the present invention is also useful for improving a visual dysfunction.

This application is based on a patent application No. 2007-112248 filed in Japan (filing date: Apr. 20, 2007), the contents of which are incorporated in full herein by this reference.

The invention claimed is:

1. A method for promoting ocular tissue neuritogenesis, comprising administering an effective amount of N-(1-acetylpiperidin-4-yl)-4-fluorobenzamide or a pharmaceutically acceptable salt thereof to a subject in need of promotion of ocular tissue neuritogenesis, wherein the resulting concentration in ocular tissue of N-(1-acetylpiperidin-4-yl)-4-fluorobenzamide or a pharmaceutically acceptable salt thereof is 0.001 nM-10 nM, thereby promoting ocular tissue neuritogenesis.

2. A method for promoting corneal neuritogenesis, comprising administering an effective amount of N-(1-acetylpiperidin-4-yl)-4-fluorobenzamide or a pharmaceutically acceptable salt thereof to a subject in need of promotion of corneal neuritogenesis, wherein the resulting concentration in ocular tissue of N-(1-acetylpiperidin-4-yl)-4-fluorobenzamide or a pharmaceutically acceptable salt thereof is 0.001 nM-10 nM, thereby promoting corneal neuritogenesis.

3. The method according to claim 2, wherein the method is used for the improvement of corneal sensitivity or treatment of dry eye or a corneal epithelial disorder.

4. A method for promoting retinal neuritogenesis, comprising administering an effective amount of N-(1-acetylpiperidin-4-yl)-4-fluorobenzamide or a pharmaceutically acceptable salt thereof to a subject in need of promotion of retinal neuritogenesis, wherein the resulting concentration in ocular tissue of N-(1-acetylpiperidin-4-yl)-4-fluorobenzamide or a pharmaceutically acceptable salt thereof is 0.001 nM-10 nM, thereby promoting retinal neuritogenesis.

5. The method according to claim 4, wherein the method is used for the improvement of a visual dysfunction.

6. The method of claim 1, wherein the resulting concentration in ocular tissue of N-(1-acetylpiperidin-4-yl)-4-fluorobenzamide or a pharmaceutically acceptable salt thereof is 0.01 nM-1 nM.

7. The method of claim 6, wherein the resulting concentration in ocular tissue of N-(1-acetylpiperidin-4-yl)-4-fluorobenzamide or a pharmaceutically acceptable salt thereof is 0.05 nM-0.5 nM.

8. The method of claim 2, wherein the resulting concentration in ocular tissue of N-(1-acetylpiperidin-4-yl)-4-fluorobenzamide or a pharmaceutically acceptable salt thereof is 0.01 nM-1 nM.

9. The method of claim 8, wherein the resulting concentration in ocular tissue of N-(1-acetylpiperidin-4-yl)-4-fluorobenzamide or a pharmaceutically acceptable salt thereof is 0.05 nM-0.5 nM.

10. The method of claim 4, wherein the resulting concentration in ocular tissue of N-(1-acetylpiperidin-4-yl)-4-fluorobenzamide or a pharmaceutically acceptable salt thereof is 0.01 nM-1 nM.

11. The method of claim 10, wherein the resulting concentration in ocular tissue of N-(1-acetylpiperidin-4-yl)-4-fluorobenzamide or a pharmaceutically acceptable salt thereof is 0.05 nM-0.5 nM.

\* \* \* \* \*